(12) United States Patent
Yang

(10) Patent No.: US 12,357,343 B2
(45) Date of Patent: Jul. 15, 2025

(54) ENDOSCOPE FOR MULTI-CHANNEL MINIMALLY INVASIVE CHANNEL

(71) Applicant: Dragon Crown Medical Co., Ltd., Jinan (CN)

(72) Inventor: Wenzhou Yang, Jinan (CN)

(73) Assignee: Dragon Crown Medical Co., Ltd., Jinan (CN)

( * ) Notice: Subject to any disclaimer, the term of this patent is extended or adjusted under 35 U.S.C. 154(b) by 629 days.

(21) Appl. No.: 17/244,950

(22) Filed: Apr. 29, 2021

(65) Prior Publication Data

US 2021/0244435 A1 Aug. 12, 2021

Related U.S. Application Data

(63) Continuation-in-part of application No. PCT/CN2018/000428, filed on Dec. 21, 2018.

(30) Foreign Application Priority Data

Nov. 1, 2018 (CN) .......................... 201821789249.5

(51) Int. Cl.
*A61B 17/34* (2006.01)
*A61B 1/00* (2006.01)
*A61B 1/12* (2006.01)
*A61B 17/00* (2006.01)

(52) U.S. Cl.
CPC ...... *A61B 17/3421* (2013.01); *A61B 1/00154* (2013.01); *A61B 1/126* (2013.01); *A61B 17/00234* (2013.01); *A61B 17/3423* (2013.01); *A61B 2017/0042* (2013.01); *A61B 2017/3447* (2013.01)

(58) Field of Classification Search
CPC . A61B 17/3421; A61B 1/00154; A61B 1/126; A61B 17/00234; A61B 17/3423; A61B 2017/0042; A61B 2017/3447; A61B 2017/3445; A61B 1/00131; A61B 1/015; A61B 1/018; A61B 1/317; A61B 1/3135
See application file for complete search history.

(56) References Cited

U.S. PATENT DOCUMENTS

| 5,749,889 A * | 5/1998 | Bacich ............... A61B 17/3421 606/198 |
| 6,352,503 B1 * | 3/2002 | Matsui ............... A61B 1/00147 600/106 |
| 2009/0292164 A1 * | 11/2009 | Yamatani ......... A61B 17/00234 600/106 |

(Continued)

FOREIGN PATENT DOCUMENTS

| CN | 108309395 A * | 7/2018 | ....... A61B 17/00234 |
| EP | 3861922 A1 | 8/2021 | |
| KR | 102532904 B1 | 5/2023 | |

*Primary Examiner* — Anh Tuan T Nguyen
*Assistant Examiner* — Shankar Raj Ghimire

(57) ABSTRACT

An endoscope including a working channel and an accessory endoscope. The working channel includes a main channel, an accessory channel, and a handle. The main channel and the accessory channel are rigidly connected to the handle. The main channel and the accessory channel each include an inlet disposed on the handle. The accessory endoscope is disposed in the accessory channel. The accessory endoscope comprises an accessory cleaning channel and an accessory optical channel; and no instrument channel is disposed in the accessory endoscope.

5 Claims, 6 Drawing Sheets

(56) References Cited

U.S. PATENT DOCUMENTS

| | | | |
|---|---|---|---|
| 2010/0261962 A1* | 10/2010 | Friedberg | A61B 1/00082 600/114 |
| 2012/0289858 A1* | 11/2012 | Ouyang | A61B 1/00101 600/562 |
| 2015/0031951 A1* | 1/2015 | Furlong | A61B 1/00133 600/106 |
| 2016/0089008 A1* | 3/2016 | Simmons | A61B 1/00128 600/106 |
| 2018/0008129 A1* | 1/2018 | Kuwae | A61B 1/3132 |
| 2019/0209811 A1* | 7/2019 | Friend | A61B 1/015 |

* cited by examiner

A - A

ENDOSCOPE FOR MULTI-CHANNEL MINIMALLY INVASIVE CHANNEL

CROSS-REFERENCE TO RELATED APPLICATIONS

This application is a continuation-in-part of International Patent Application No. PCT/CN2018/000428 with an international filing date of Dec. 21, 2018, designating the United States, now pending, and further claims foreign priority benefits to Chinese Patent Application No. 201821789249.5 filed Nov. 1, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to the field of surgical instrument and equipment, and more particularly to an endoscope for multi-channel minimally invasive channel.

Minimally invasive surgery refers to a surgery performed by use of modern medical instruments such as laparoscope or thoracoscope, as well as a minimally invasive channel device and related equipment.

In minimally invasive techniques, a transforaminal endoscope may be used. The transforaminal endoscope includes an external sleeve and an endoscope provided inside the sleeve. The traditional endoscope is provided with a cleaning channel, an optical channel, an instrument channel, and an optical fiber therein. The optical channel is used to place a camera therein, such that an operator can observe the circumstance of an operation site. A surgical instrument is placed inside the instrument channel. However, the traditional scheme has the following shortcomings.

1. The surgical instruments are different in size; the small-sized instrument is insufficient in mechanical strength, and the large-sized instrument cannot be inserted into the instrument channel smoothly and can only be used individually.

2. The optical channel is fixed on one side of the instrument channel, so that there is a blind spot in the case of observing the operation of the instrument.

SUMMARY

The objective of the disclosure is to provide an endoscope for a multi-channel minimally invasive channel, which can assist in observation when the endoscope is working.

The disclosure provides an endoscope for a multi-channel minimally invasive channel. The endoscope comprises a working channel and an accessory endoscope; the working channel comprises a main channel, an accessory channel and a handle; the main channel and the accessory channel are rigidly connected to the handle; the main channel and the accessory channel each comprise an inlet disposed on the handle; the accessory endoscope is disposed in the accessory channel; the accessory endoscope comprises an accessory cleaning channel and an accessory optical channel; and no instrument channel is provided in the accessory endoscope. The accessory endoscope disposed in the accessory channel has an observation function, that is, accessory endoscope can replace an observation function of the main channel and can also play an auxiliary role.

In a class of this embodiment, the length of the main channel is greater than that of the accessory channel. The main channel is longer, thereby preventing equipment in the accessory channel from affecting the main channel.

In a class of this embodiment, the main channel and the accessory channel are arranged at an acute angle, and the main channel and the accessory channel are attached at the outlets thereof and separated at the inlets thereof. Attachment at the outlets can save the operation space.

In a class of this embodiment, an endoscope view hole is provided in one side of the main channel outlet, and is located between the main channel outlet and the accessory channel outlet. The endoscope view hole is used for observation of a main endoscope and the accessory endoscope.

In a class of this embodiment, the main channel, the accessory channel and the handle are of an integrated structure, and the main channel and the accessory channel are connected by a reinforcing rib.

In a class of this embodiment, the main channel outlet communicates with the endoscope view hole, such that a range of observation can be enlarged.

In a class of this embodiment, the main endoscope is disposed in the main channel, and a main cleaning channel, a main optical channel and a main instrument channel are disposed in the main endoscope. The main endoscope adopts a traditional structure, and the accessory endoscope can assist in observation.

In a class of this embodiment, a surgical instrument is disposed in the main channel. A large-sized surgical instrument can be placed in the main channel, and the accessory endoscope has observation and cleaning functions instead of the original main endoscope.

In a class of this embodiment, the diameter of the main channel is greater than that of the accessory channel. Since there are no instruments provided in the accessory channel, the diameter of the accessory channel is relatively small, such that a space can be saved.

The following advantages are associated with the endoscope of the disclosure:

1. Different transforaminal endoscopes can be placed in the main channel and the accessory channel respectively, and the operation site can be observed from multiple angles during the surgical operation.

2. Large-sized instruments can be placed in the main channel, such that instruments with higher strength can be used with a wider range of adaptation.

3. The accessory endoscope is specially used for observation during operation, and is not equipped with surgical instruments, so the volume is smaller and the space is saved.

Figure 1:
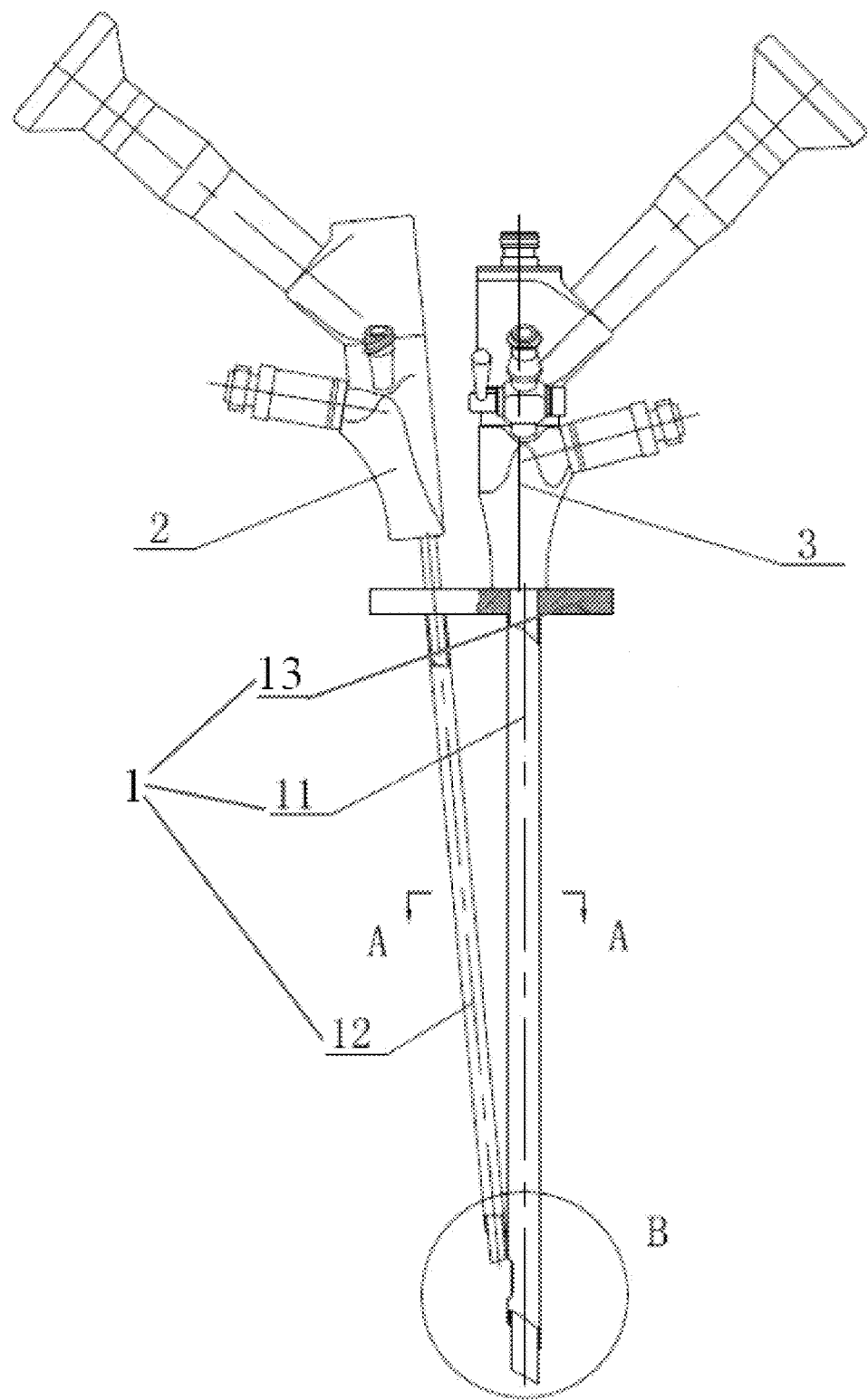
FIG. 1 is a schematic diagram of an endoscope in accordance with one embodiment of the disclosure.
Figure 2:
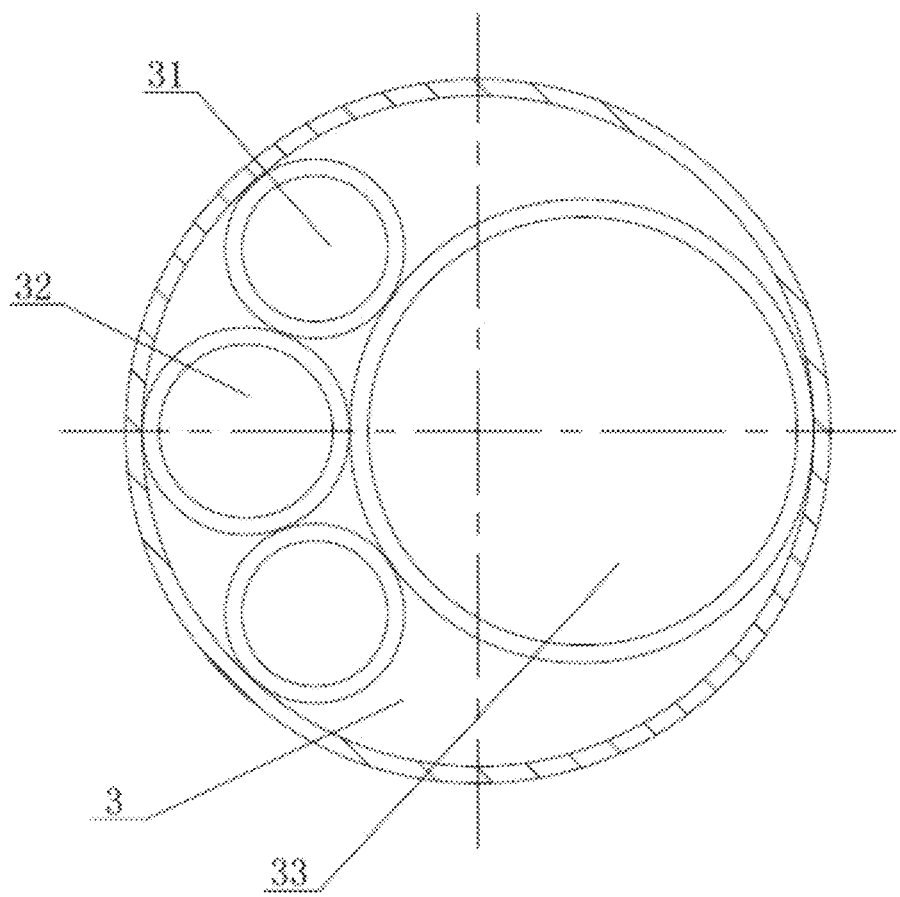
FIG. 2 is a sectional view of a main endoscope of an endoscope in accordance with one embodiment of the disclosure.
Figure 3:
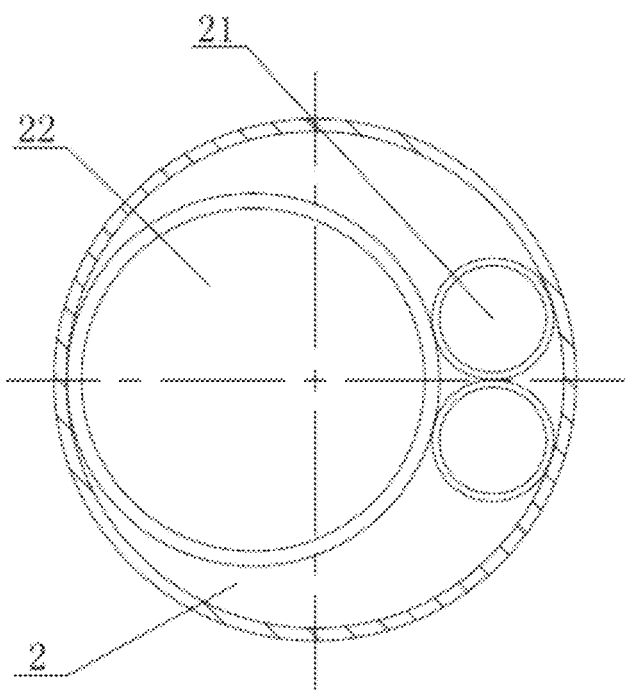
FIG. 3 is a sectional view of an accessory endoscope of an endoscope in accordance with one embodiment of the disclosure.
Figure 4:
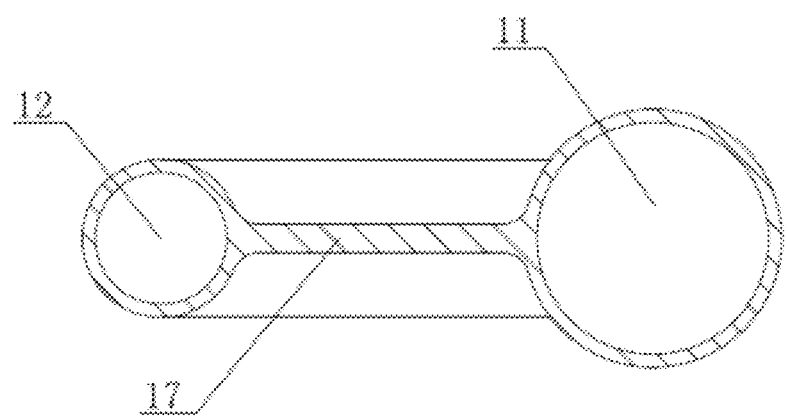
FIG. 4 is a sectional view of a working channel taken from line A-A in FIG. 1.
Figure 5:
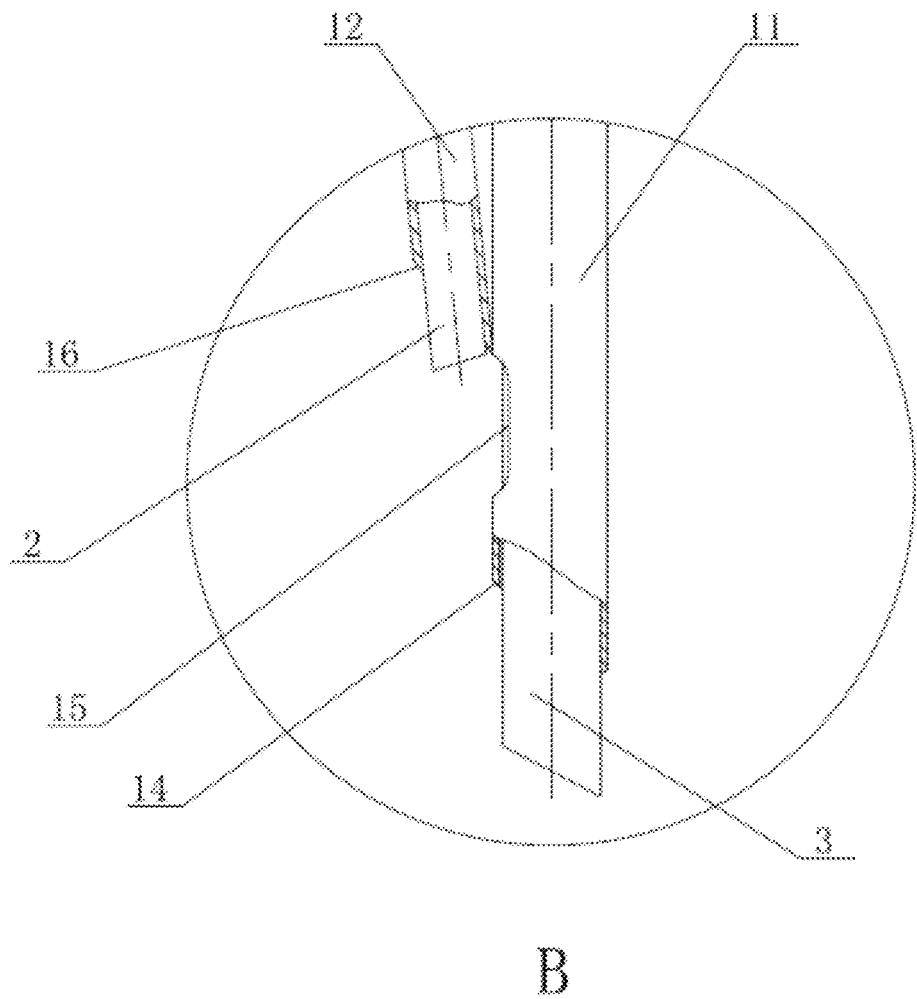
FIG. 5 is an enlarged drawing of a part B of FIG. 1 in accordance with Example 1.

In the drawings, the following reference numbers are used: 1: Working channel; 2: Accessory endoscope; 3: Main endoscope; 4: Surgical instrument; 11: Main channel; 12: Accessory channel; 13: Handle; 14: Main channel outlet; 15: Endoscope view hole; 16: Accessory channel outlet; 17: Reinforcing rib; 21: Accessory cleaning channel; 22: Accessory optical channel; 31: Main cleaning channel; 32: Main optical channel; 33: Main instrument channel.

DETAILED DESCRIPTION

To further illustrate, embodiments detailing an endoscope for multi-channel minimally invasive channel are described below. It should be noted that the following embodiments are intended to describe and not to limit the disclosure.

Example 1

As shown in FIGS. 1-5, provided is an endoscope for a multi-channel minimally invasive channel. The endoscope comprises a working channel 1, an accessory endoscope 2, and a main endoscope 3. The working channel 1 comprises a main channel 11, an accessory channel 12 and a handle 13 which are integrally provided; the main channel 11 and the accessory channel 12 are connected to the handle 13, and the main channel 11 and the accessory channel 12 each comprise an inlet disposed on the handle 13. One end of the main channel 11 away from the handle 13 is provided with a main channel outlet 14 and an endoscope view hole 15, and the accessory channel 12 is also provided with an accessory channel outlet 16. The endoscope view hole 15 is disposed at one side of the main channel outlet 14, and is located between the main channel outlet 14 and the accessory channel outlet 16. The main channel 11 and the accessory channel 12 are arranged at an acute angle, and are separated at their inlets and tightly attached at their outlets, that is, the accessory channel outlet 16 is closely attached to the main channel 11. The length of the main channel 11 is greater than that of the accessory channel 12.

The main channel 11 and the accessory channel 12 are also connected via a reinforcing rib 17.

The main endoscope 3 is of a traditional endoscope structure, and is provided with a main cleaning channel 31, a main optical channel 32, and a main instrument channel 33 therein. The accessory endoscope 2 comprises an accessory cleaning channel 21 and an accessory optical channel 22 therein, and no instrument channel is provided inside the accessory endoscope 2. The main endoscope 3 is disposed in the main channel 11, and the accessory endoscope 2 is disposed in the accessory channel 12.

The working principle of the endoscope of the disclosure is as follows: during working, the main endoscope 3 and the accessory endoscope 2 are placed in the main channel 11 and the accessory channel 12 respectively, and this endoscope device is then used for a surgical operation. Both the main endoscope 3 and the accessory endoscope 2 have optical channels and can be switched for observation.

Example 2

Figure 6:
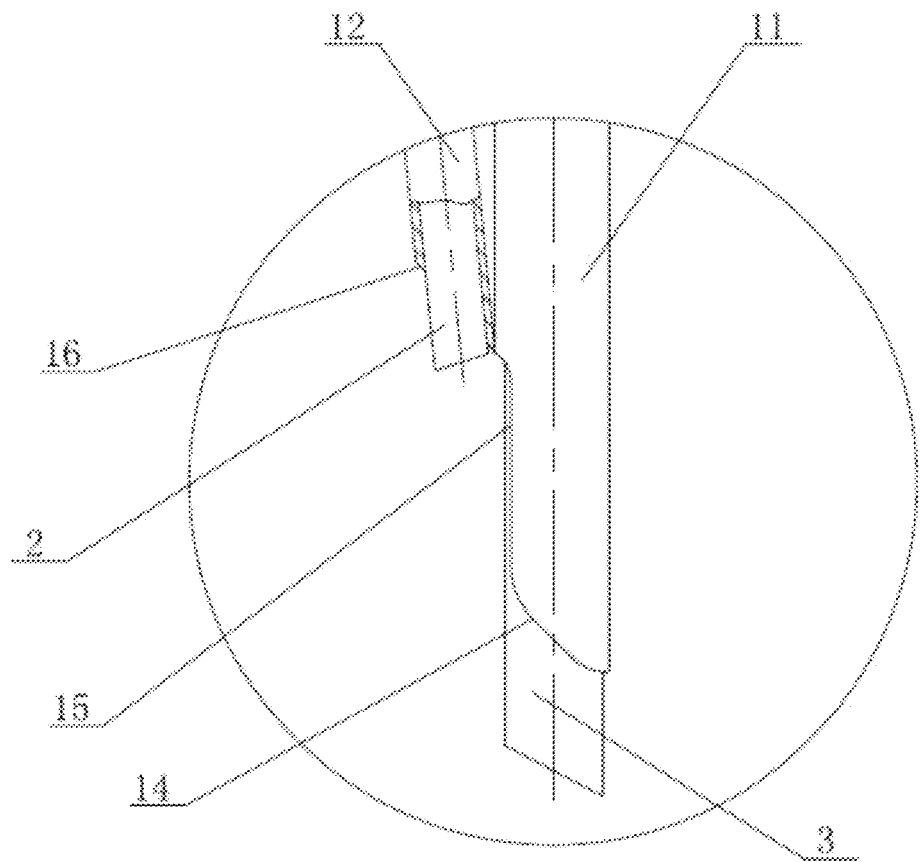
FIG. 6 is an enlarged drawing of a part B of FIG. 1 in accordance with Example 2.

As shown in FIG. 6, in this example, the endoscope view hole 15 and the main channel outlet 14 are integrally provided, which can increase range of motion of an instrument and facilitate observation of the instrument by the accessory endoscope 2. The other parts of this example are basically the same as that in Example 1.

Example 3

Figure 7:
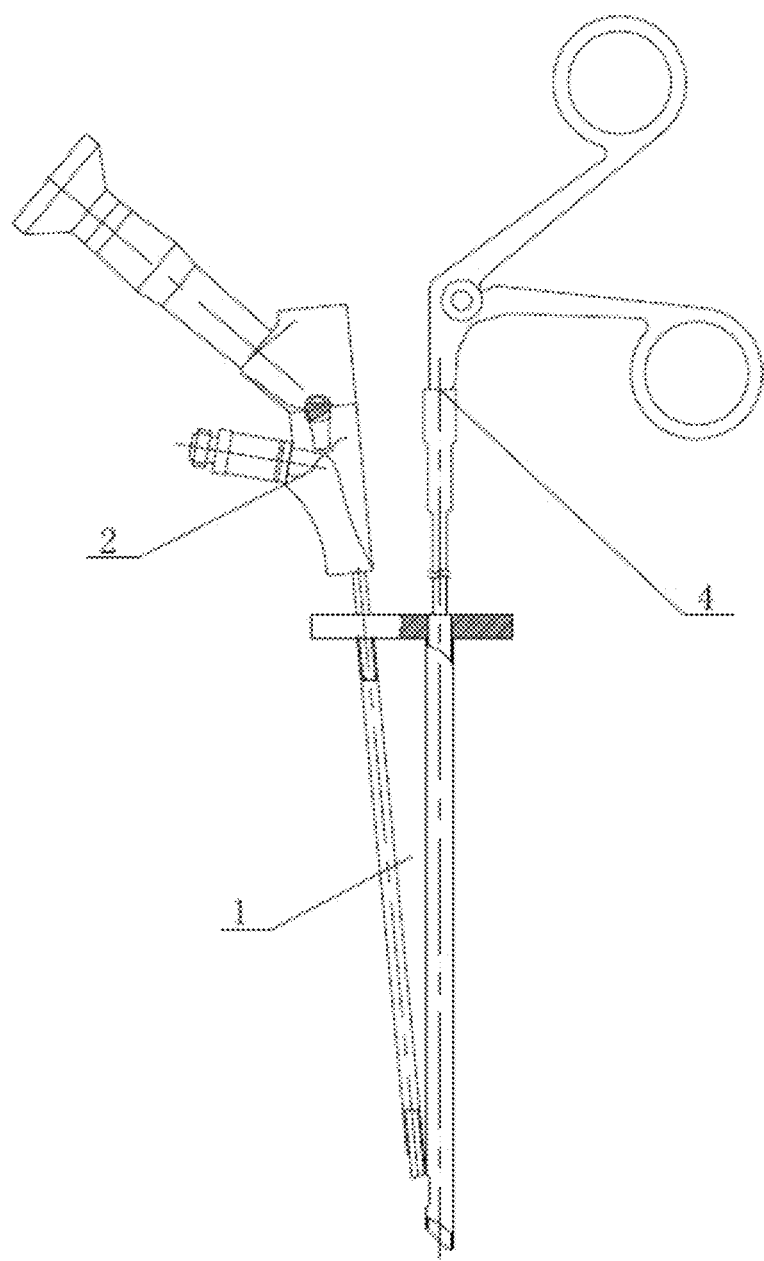
FIG. 7 is a schematic diagram of an endoscope in Example 3.

As shown in FIG. 7, in this example, a surgical instrument 4, rather than the main endoscope 3, is directly placed in the main channel 11. Therefore, a larger-sized instrument can be directly used, which increases the versatility in case of the channel diameter being inconvenient. The accessory endoscope 2 can also be used for cleaning and image observation. The other parts of this example are basically the same as that in Example 1.

It will be obvious to those skilled in the art that changes and modifications may be made, and therefore, the aim in the appended claims is to cover all such changes and modifications.

What is claimed is:

1. A device comprising: a working channel, a main endoscope and an accessory endoscope, wherein the working channel comprises a main channel, an accessory channel, and a handle; the main channel and the accessory channel are rigidly connected to the handle; the main channel and the accessory channel each comprise an inlet disposed on the handle; the accessory endoscope is disposed in the accessory channel; the accessory endoscope comprises an accessory cleaning channel and an accessory optical channel that are disposed in the accessory endoscope; the main endoscope is disposed in the main channel, and the main endoscope comprises a main cleaning channel, a main optical channel and a main instrument channel;

wherein an endoscope view hole is disposed at one side of a main channel outlet, and located between the main channel outlet and an accessory channel outlet; and the main channel outlet communicates with the endoscope view hole;

wherein an inlet end of the main channel and an inlet end of the accessory channel are spaced apart from each other, and an outlet end of the accessory channel and proximal side of the endoscope view hole are in close contact with each other, such that the main channel and the accessory channel are arranged at an acute angle relative to each other, with a vertex of the acute angle being a point where the outlet end of the accessory channel and the proximal side of the endoscope view hole are in contact.

2. The device of claim 1, wherein a length of the main channel is greater than that of the accessory channel.

3. The device of claim 1, wherein the main channel, the accessory channel and the handle are of an integrated structure, and the main channel and the accessory channel are connected via a reinforcing rib.

4. The device of claim 1, wherein a surgical instrument is disposed in the main channel.

5. The device of claim 1, wherein a diameter of the main channel is greater than that of the accessory channel.

\* \* \* \* \*